United States Patent
Koh

(10) Patent No.: US 7,493,164 B1
(45) Date of Patent: Feb. 17, 2009

(54) APPLICATION OF BLOOD PRESSURE PROFILE PARAMETER TO ASSESS CIRCADIAN STATE OF PATIENTS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 550 days.

(21) Appl. No.: 11/237,379

(22) Filed: Sep. 27, 2005

(51) Int. Cl.
*A61N 1/365* (2006.01)
(52) U.S. Cl. .................... 607/23; 600/486; 600/508
(58) Field of Classification Search ............ 607/23
See application file for complete search history.

(56) References Cited

U.S. PATENT DOCUMENTS

| | | | |
|---|---|---|---|
| 4,712,555 A | 12/1987 | Thornander et al. ... | 128/419 PG |
| 4,940,052 A | 7/1990 | Mann et al. .......... | 128/419 PG |
| 5,143,065 A | 9/1992 | Adkins et al. ......... | 128/419 PG |
| 5,466,254 A | 11/1995 | Helland ................ | 607/123 |
| 5,476,483 A | 12/1995 | Bornzin et al. ........ | 607/17 |
| 5,626,623 A | 5/1997 | Kieval et al. .......... | 607/23 |
| 5,733,312 A | 3/1998 | Schloss et al. ........ | 607/17 |
| 5,861,011 A | 1/1999 | Stoop ................. | 607/25 |
| 6,128,534 A | 10/2000 | Park et al. ........... | 607/17 |
| 6,731,984 B2 | 5/2004 | Cho et al. ............ | 607/17 |
| 7,367,951 B2* | 5/2008 | Bennett et al. ........ | 600/485 |
| 2002/0138009 A1* | 9/2002 | Brockway et al. ..... | 600/485 |
| 2004/0077953 A1 | 4/2004 | Turcott .............. | 600/483 |
| 2004/0147969 A1 | 7/2004 | Mann et al. .......... | 607/17 |

FOREIGN PATENT DOCUMENTS

| EP | 0 392 800 B1 | 6/1994 |
|---|---|---|
| EP | 1 410 756 A1 | 4/2004 |

* cited by examiner

*Primary Examiner*—Kennedy J Schaetzle

(57) ABSTRACT

A monitoring and/or stimulation device to receive a signal from a lead sensor positioned in the heart of patient. The monitoring and/or stimulation device processes the blood pressure data received from the sensor to determine an augmentation pressure for each heart beat. The augmentation pressure may be tracked over time or compared to a template to determine the circadian state of the patient. The augmentation pressure may be tracked or analyzed over a longer time period to detect other heart conditions such as hypertension.

11 Claims, 6 Drawing Sheets

APPLICATION OF BLOOD PRESSURE PROFILE PARAMETER TO ASSESS CIRCADIAN STATE OF PATIENTS

TECHNICAL FIELD

This application relates generally to implantable cardiac monitoring and stimulation devices and, more specifically, to a monitoring and stimulation apparatus and method that uses blood pressure measurements to determine the circadian state of a patient and various heart conditions.

BACKGROUND

A conventional pacemaker stimulates a patient's heart to maintain regular contractions of the heart thereby promoting blood circulation within the patient. Such stimulation may be prescribed when the patient's heart does not function normally due to, for example, a genetic condition.

In a healthy heart, contractions occur first in the muscles associated with the atria of the heart, followed by contractions in the muscles associated with the larger ventricles of the heart. In this way, atria chambers assist in the filling of ventricle chambers with blood returning from the veins. This enables the ventricles to more efficiently pump blood to the arteries.

Given the interaction of these chambers, efficient operation of the heart is predicated on each of the chambers operating in a proper timing sequence and having contractions that pump a sufficient amount of blood from each chamber. For example, during contraction the right atrium chamber should pump enough blood to effectively "fill" the right ventricle chamber. Moreover, this should occur immediately before the right ventricle begins to contract. In this way, the heart may efficiently pump blood on a repetitive basis.

A healthy heart repetitively contracts in the above described manner in response to the generation and conduction of electrical signals in the heart. These electrical signals are generated in and conducted through the heart during every beat of the heart.

Under certain circumstances, a pacemaker may compensate for abnormal operation of a heart by pacing (e.g., stimulating) one or more of the atria and/or ventricles. To stimulate the heart, a typical pacemaker generates a series of electrical signals which are applied to the heart via one or more electrodes implanted in the heart (e.g., in ventricular or atrial chambers). These electrical signals cause the heart to contract in much the same way as the native electrical signals discussed above cause the heart to contract.

To provide appropriate timing for the generation of electrical signals, conventional pacemakers may sense signals in the heart. For example, a pacemaker may sense electrical signals in the atria to detect when the atria are being activated. The pacemaker may then delay a prescribed period of time after which it senses electrical signals in the ventricles or atria to determine whether to apply a stimulus to the ventricles or atria. In this way, the pacemaker may stimulate the ventricles or atria at the appropriate time, if necessary, in an attempt to maintain efficient operation of the heart.

The signals from the sensors in the heart may be collected in the pacemaker to be further analyzed to determine when a stimulus should be generated or other action taken. For example, the data received from the sensors may be stored as a time series of data. The time series includes an indicator of the time a sample of data was taken and a value such as amplitude of the signal at that time. This time series data may then be processed by an appropriate circuit and/or analyzed by morphology detection algorithms and arrhythmia detection algorithms to determine the timing of the electrical pulses to pace the heart.

The appropriate pulse generation timing is not dependent entirely on the detection of other cardiac signals. That is, optimum timing may not result from simply detecting the activation of the atria and then waiting a prescribed amount of time before generating a pulse to stimulate the ventricles. The timing and characteristics of the electrical signal in the heart are affected by the overall state of the heart and the activity of the patient. For example, the timing and characteristics of signals in the heart differ between an awakened state and a sleep state and between a resting state and an active state. Correct tracking and determination of the state of the patient improves the efficiency and accuracy of the signaling of the pacemaker and consequently improves the function of the heart.

SUMMARY

The embodiments of the invention relate to a method and apparatus for processing blood pressure data received from a lead sensor or multiples sensors in the heart. The blood pressure data and related data collected from the set of sensors in the leads implanted in or near the heart are analyzed to determine an augmentation pressure measurement and similar information for each beat of the heart.

The augmentation pressure is a subset of the blood pressure data measured in the heart corresponding to an increase in blood pressure that occurs in the heart during its normal pumping function. The augmentation pressure may be tied to an increase in blood pressure in the heart as a result of the filling of the ventricles and the subsequent pumping of blood out of the ventricles. The augmentation pressure has a relationship with baro-receptor sensitivity, which is an indicator of arterial wall flexibility. Wall flexibility increases during sleep state and continuous inflexibility is caused by hypertension. The augmentation pressure may be monitored as a surrogate for the baro-receptor sensitivity to detect or confirm a circadian state of the patient. The augmentation pressure monitoring over longer periods of time may also be used to detect other heart conditions such as hypertension.

The monitored augmentation pressure data may be tracked over short and long periods of time. The monitoring device may be trained or set for the particular heart conditions of a patient. The short term monitoring may compare augmentation pressure measurements over time with predetermined or dynamic threshold levels. The threshold levels indicate the difference in expected augmentation pressure levels for each circadian state of the patient or other heart conditions.

In other embodiments of short term monitoring, the measured augmentation data may be processed as a histogram or similarly statistically analyzed. The histogram of measured augmentation pressure may be compared to a template to detect changes in the circadian state or other heart conditions.

Other types of conditions may be detected or confirmed through analysis of short term augmentation data. For example, sleep apnea that is detected by monitoring of the respiratory state of a patient may be confirmed through the analysis of the short term data and accurate tracking of the circadian state of the patient using the data.

In one embodiment, the tracking of augmentation pressure over a longer term may be used to detect or confirm hypertension in the patient. If increases in augmentation pressure in both awake and sleep states is maintained over a predetermined period of time then hypertension may be the cause. The monitoring device may generate an indicator or other alarm mechanism to alert the patient or medical personnel of the condition. Other heart conditions may also be detected by analysis of long term data such as hypotension.

BRIEF DESCRIPTION OF THE DRAWINGS

These and other features, aspects and advantages of the invention will be more fully understood when considered with respect to the following detailed description, appended claims and accompanying drawings, wherein:

Figure 1:
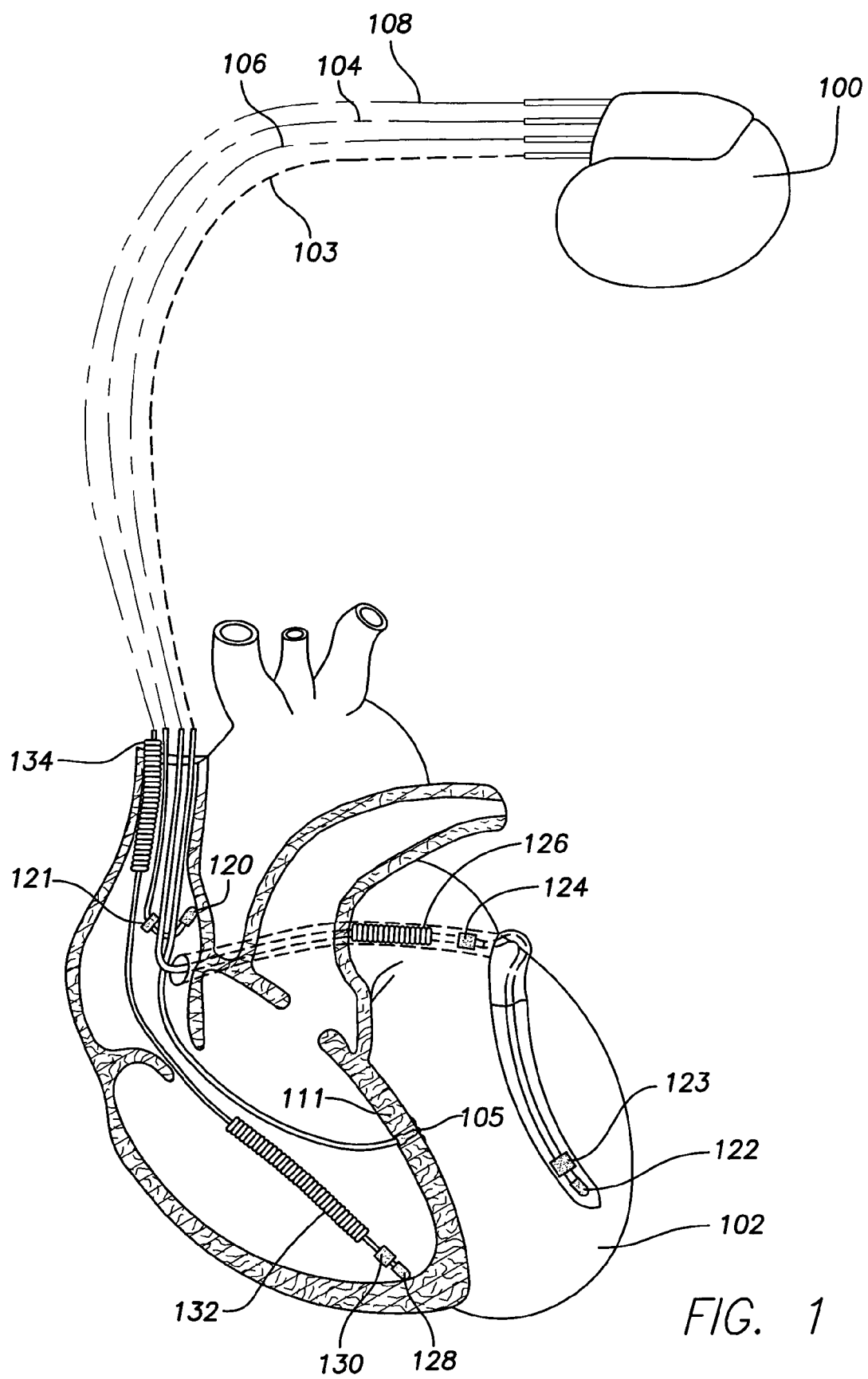
FIG. 1 is a simplified diagram of one embodiment of an implantable monitoring and/or stimulation device in electrical communication with a set of leads implanted in a patient's heart.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

The following description sets forth but one exemplary heart monitoring and/or stimulation device that is capable of being used in connection with the various embodiments that are described below. It is to be appreciated and understood that other monitoring and/or stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of set of leads 103, 104, 106, and 108, suitable for delivering multichamber stimulation and shock therapy, as well as carrying sensors for measuring heart conditions in various locations throughout the heart. As used herein, a set may refer to any number of related items including a single item.

To sense atrial cardiac signals and to provide right atrial chamber stimulation therapy, monitoring device 100 is coupled to an implantable right atrial lead 104 having, for example, an atrial tip electrode 120, which typically is implanted in the patient's right atrial appendage or septum. FIG. 1 shows the right atrial lead 104 as having an optional atrial ring electrode 121. The right atrial lead may also include and incorporate other types of sensors including blood pressure sensors. The sensors utilized for determining aortic blood pressure may include piezo-electric sensors, tribo-electric sensors and similar sensor types. For example, a cardiomechanic sensor (CMES) or similar device may be placed in the lead 104.

To sense left atrial and ventricular cardiac signals and to provide left chamber pacing therapy, monitoring device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. The left atrial and ventricular lead may also include and incorporate other types of sensors including blood pressure sensors. The sensors utilized for determining aortic and ventricular blood pressure may include piezo-electric sensors, tribo-electric sensors and similar sensor types. For example, a CMES or similar device may be placed in the lead 106.

An exemplary coronary sinus lead 106 is designed to receive atrial and ventricular cardiac signals and to deliver left ventricular pacing therapy using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Monitoring and/or stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. The right ventricular lead 108 may also include and incorporate other types of sensors including blood pressure sensors. The sensors utilized for determining ventricular blood pressure may include piezo-electric sensors, tribo-electric sensors and similar sensor types. For example, a cardio-mechanic sensor (CMES) or similar device may be placed in the lead 104. In one embodiment, a blood pressure sensor may be placed in the right ventricular apex to measure blood pressure at the apex of the right ventricle.

In some embodiments, a trans-septal lead 103 may be present to place a sensor device 105 into the left ventricle. The trans-septal lead 103 may be disposed partially in the right ventricle and through the septal wall 111. The profile of the sensor 105 may be low against the septal wall to minimize or prevent clotting on the surface of the sensor 105 or the mounting mechanism. The trans-septal lead 103 may also include and incorporate any type of sensor including blood pressure sensors. The sensors utilized for determining ventricular blood pressure may include piezo-electric sensors, tribo-electric sensors and similar sensor types. For example, a cardio-mechanic sensor (CMES) or similar device may be placed in the lead 103.

In further embodiments, sensor devices may be positioned in other areas of the heart or body. The sensors may be in communication with the monitoring and/or stimulation device 100 to provide data for use in pacing and health condition monitoring. The sensors may communicate with the monitoring and/or stimulation device 100 through wire, wireless, optical or similar communications mediums. In one embodiment, sensors may be placed in any portion of the body to detect blood pressure levels where the augmentation pressure exhibits the same characteristics and relationships as augmentation pressure in the heart.

Figure 2:
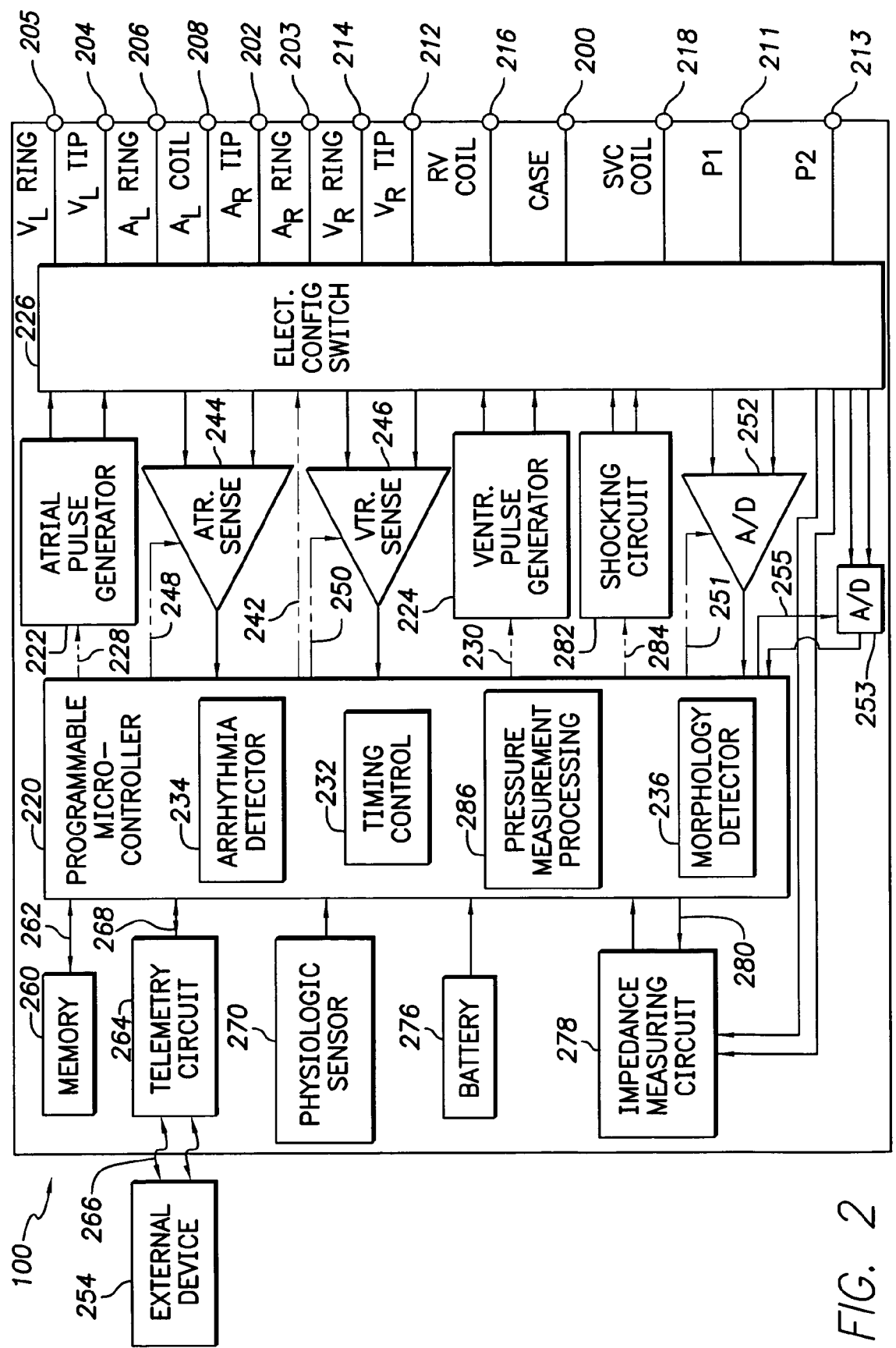
FIG. 2 is a simplified functional block diagram of one embodiment of a multi-chamber implantable stimulation device constructed in accordance with the invention, illustrating basic elements that are configured to track, analyze and store augmentation pressure data as well as provide cardioversion, defibrillation or pacing stimulation or any combination thereof.

FIG. 2 shows an exemplary, simplified block diagram depicting various components of the monitoring and/or stimulation device 100. The monitoring and/or stimulation device 100 can be capable of treating both fast and slow arrhythmias with stimulation therapy, including cardioversion, defibrillation, and pacing stimulation. The monitoring and/or stimulation device 100 also gathers and analyzes sensor data received from sensors in the leads. While a particular multi-chamber device is shown, it is to be appreciated and understood that this is done for illustration purposes only. Thus, the techniques and methods described below can be implemented in connection with any suitably configured or configurable monitoring and/or stimulation device 100. Accordingly, one of skill in the art could readily duplicate, eliminate, or disable the appropriate circuitry in any desired combination to provide a device capable of treating the appropriate chamber(s) with cardioversion, defibrillation, and pacing stimulation or detecting different heart conditions including circadian state and hypertension.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 203, 204, 205, 206, 208, 212, 214, 216, and 218 (shown schematically and, for convenience, the names of the electrodes to which they are connected are shown next to the terminals).

In some embodiments, device 100 also may include circuitry for processing signals from one or more pressure sensors that may be attached to any of the leads and in place throughout the heart or other locations. Depending upon the application, the pressure sensors may be implanted in the heart, in other locations in the patient such as the thoracic cavity, anywhere along a lead or within the housing 200.

A typical pressure sensor generates electrical signals indicative of changes in a sensed pressure type. Thus, one or more wires may be used to connect a sensor to the device 100. FIG. 2 illustrates an example embodiment where two pressure signals P1 and P2 are coupled to the device 100 via terminals 211 and 213, respectively.

To achieve right atrial sensing and pacing, the connectors may further include, for example, a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes, for example, a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the monitoring and/or stimulation device 100 is a programmable microcontroller 220 that controls the various modes of stimulation therapy and processes received data from sensors. As is well known in the art, microcontroller 220 typically includes a microprocessor, or equivalent control circuitry, designed specifically for controlling the delivery of stimulation therapy and the analysis of sensor data. The microcontroller 220 may further include RAM or ROM memory, logic and timing circuitry, state machine circuitry, and I/O circuitry. Typically, microcontroller 220 includes the ability to process or monitor input signals (data or information) as controlled by a program code stored in a designated block of memory 260 external to the microcontroller or embedded in the microcontroller 220. The type of microcontroller 220 is not critical to the described implementations. Rather, any suitable microcontroller 220 may be used that carries out the functions described herein. The use of microprocessor-based control circuits for performing timing and data analysis functions are well known in the art. Microcontroller 220 may be a general purpose programmable microcontroller or an application specific integrated circuit or a combination thereof.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 may further include an arrhythmia detector 234, a morphology detector 236, pressure measurement processing component 286, and optionally an orthostatic compensator and a minute ventilation (MV) response module, the latter two are not shown in FIG. 2. These components can be utilized by the monitoring and/or stimulation device 100 for determining desirable times to administer various therapies, including those to reduce the effects of orthostatic hypotension. For example, the pressure measurement processing component 286 may execute an algorithm that tracks augmentation blood pressure in the heart over time and detects the circadian state of patient. The pressure measurement processing component 286 may also play a role in detecting or confirming hypertension, sleep apnea and similar heart or other conditions. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

In one embodiment, the device 100 may include an analog-to-digital (A/D) data acquisition system 253 that may be configured (e.g., via signal line 255) to acquire and amplify the signals P1 and P2, convert the raw analog data into a digital signal, filter the signals and store the digital signals for later processing by, for example, a pressure measurement processing component 286 and/or telemetric transmission to an external device 254.

The microcontroller 220 is further coupled to a memory 260 by a suitable data/address bus 262, wherein the programmable operating parameters used by the microcontroller 220 are stored and modified, as required, in order to customize the operation of the monitoring and/or stimulation device 100 to suit the needs of a particular patient. Such operating parameters define, for example, blood pressure histogram templates, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device. For example, blood pressure data may be tracked and analyzed over the course of minutes, hours, days, months or over longer periods of time.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The monitoring and/or stimulation device 100 can further include a physiologic sensor 270, commonly referred to as a "rate-responsive" sensor because it is typically used to adjust pacing stimulation rate according to the exercise state of the patient. However, the physiologic sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the monitoring and/or stimulation device 100 separate from the microcontroller 220, it is to be understood that the physiologic sensor 270 may also be external to the stimulation device 100, yet still be implanted within or carried by the patient or may be software/firmware that is executed by the microcontroller 220 and stored. Examples of physiologic sensors that may be implemented in device 100 include known sensors that, for example, sense respiration rate, pH of blood, ventricular gradient, oxygen saturation, blood pressure and so forth. Another sensor that may be used in conjunction with the other sensors is one that detects activity variance, wherein an activity sensor is monitored diurnally to detect the low variance in the measurement corresponding to the sleep state. For a more detailed description of an activity variance sensor, the reader is directed to U.S. Pat. No. 5,476, 483 (Bornzin et al.), issued Dec. 19, 1995, which patent is hereby incorporated by reference.

More specifically, the physiologic sensors 270 optionally include sensors to help detect movement and minute ventilation in the patient. The physiologic sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down. The information from these sensors may be used in combination with blood pressure measurement sensors and data to determine or confirm the circadian state of the patient.

The monitoring and/or stimulation device additionally includes a battery 276 that provides operating power to all of the circuits shown in FIG. 2. For the monitoring and/or stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The monitoring and/or stimulation device 100 can further include magnet detection circuitry (not shown), coupled to the microcontroller 220, to detect when a magnet is placed over the device 100. A magnet may be used by a clinician to perform various test functions of the device 100 and/or to signal the microcontroller 220 that the external programmer 254 is in place to receive or transmit data to the microcontroller 220 through the telemetry circuits 264.

The monitoring and/or stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the monitoring and/or stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through, for example, two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
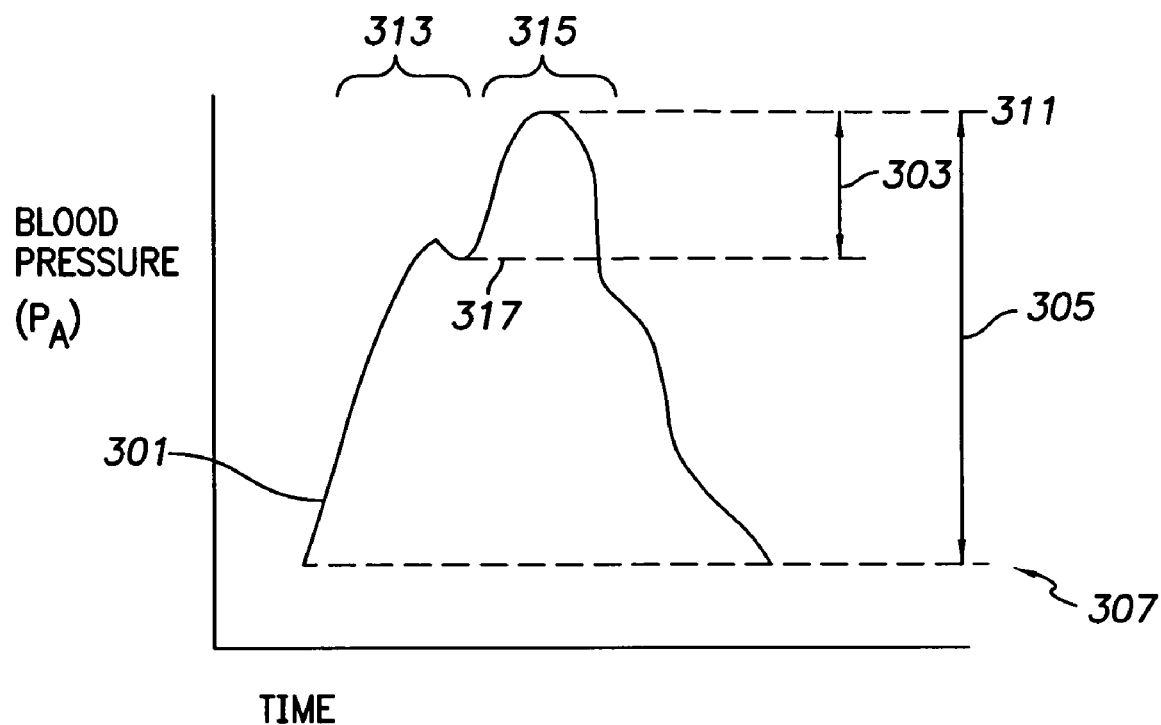
FIG. 3 is a diagram illustrating a standard blood pressure pulse during a beat of the heart of a patient.

FIG. 3 is a diagram of a signal 301 from a sensor detecting blood pressure. In one embodiment, the signal illustrated may be from the apex or central aortic space of the heart of a patient with an implanted lead sensor. The time frame of the diagram is a single beat of the heart. The diagram generally illustrates a pattern in the blood pressure in these regions of the heart. The blood pressure pattern results in a wave that increases from a baseline level 307 to a peak level over the course of time of the single beat of the heart resulting in a blood pressure pulse. The general pattern of the diagram repeats with each heart beat having a corresponding blood pressure pulse that may be detected by a lead sensor.

The pattern of blood pressure pulse for the apex, central aortic and similar regions of the heart includes an initial spike 313 of increased blood pressure corresponding to the action of the atria to pump blood into the ventricles and a second spike 315 of increased blood pressure corresponding to the action of the ventricles to pump blood out of the heart. The actual blood pressure ($P_A$) across the pulse varies from patient to patient dependent on the unique characteristics of each patient's heart. However, the general blood pressure pulse pattern is present in each patient when the heart functions in a normal manner.

The difference between the baseline 307 and the peak 311 blood pressure represents the maximum change in relative pressure 305. The difference between the local minima 317 after the first spike 313 and the peak 311 may be referred to as the augmentation pressure 303. The augmentation pressure 303 has a correlation with the wall firmness in the heart and baro-receptor sensitivity and may be used as a surrogate indicator for baro-receptor sensitivity. The augmentation pressure 303 during a sleep state is greater than when in a wakened state. That is, the difference in the blood pressure at the local minima 317 after the first blood pressure spike 313 and the peak 311 of the second blood pressure spike 315 is greater in the sleep state than in the wakened state. The difference between the augmentation pressure 303 in a wakened state and sleep state depends on the unique characteristics of each patient's heart. Generally, the augmentation pressure 303 in the sleep state is more than double the augmentation pressure 303 in a wakened state. Similarly, prolonged and consistent reduced augmentation pressure 303 in a patient may be an indicator of hypertension. Other heart conditions may also be detected or confirmed using augmentation pressure due to its relationship with baro-receptor sensitivity and wall firmness.

Thus, augmentation pressure 303 may be tracked to determine or confirm a circadian state of a patient, sleep apnea, hypertension and similar heart conditions. The accuracy of augmentation pressure 303 as an indicator for these conditions has been confirmed through testing and observation. As discussed above, augmentation pressure 303 is related to baro-receptor sensitivity in the patient. Baro-receptor sensitivity displays a similar pattern to the augmentation pressure 303, but is more difficult to monitor.

Figure 4:
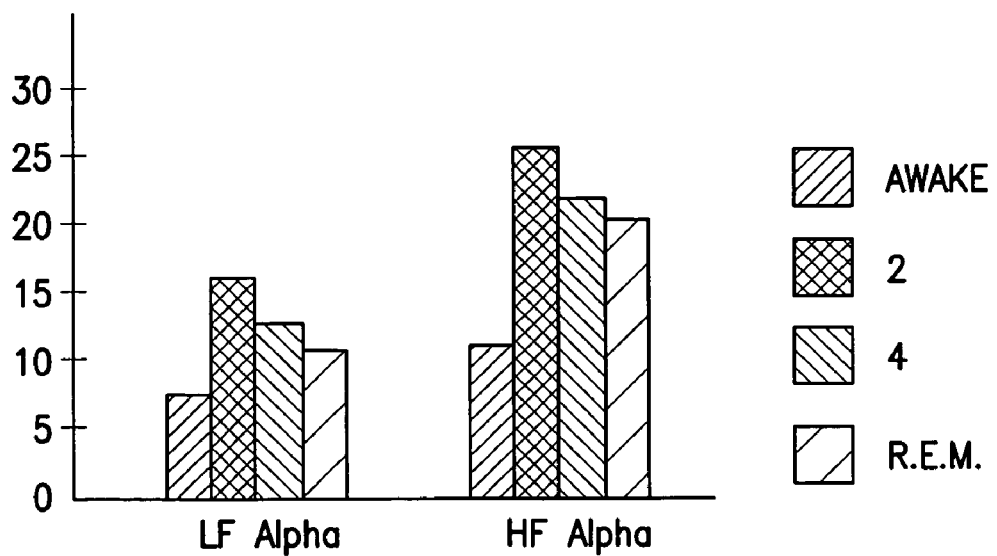
FIG. 4 is a diagram illustrating baro-receptor sensitivity during different circadian states.

FIG. 4 is a diagram showing an exemplary set of data representing low frequency (LF) alpha brainwave activity and high frequency (HF) alpha brainwave activity in different circadian states (awake, 2, 4 and REM). This diagram indirectly demonstrates the relationship between the baro-receptor sensitivity as monitored through the proxy of LF alpha and HF alpha brainwaves. The awake state has a baro-receptor sensitivity of less than half of any of the sleep states (2, 4 and REM). The determination of normal baro-receptor sensitivity and by extension augmentation pressure in sleeping and awakened states allows for the detection of these states by measurement or tracking of the current augmentation pressure of the patient.

Augmentation pressure during the sleeping state is typically significantly greater than in the awakened state for all patients. However, each individual patient has a different standard augmentation pressure in each of the circadian states. The standard augmentation pressure in each patient is readily detectible by monitoring of the augmentation pressure data received from one or more sensors (e.g., lead sensors) during a calibration or initial observation period. The monitoring and/or stimulation device may collect this data to allow a doctor or similar medical professional to determine the settings for the monitoring and/or stimulation device. Individualized settings improve the accuracy of the monitoring and/or stimulation device in detecting circadian state, hypertension, sleep apnea and similar heart conditions.

After baseline or standard blood pressure and augmentation pressure conditions have been calibrated for a patient in different states of activity, the monitoring by the monitoring and/or stimulation device for various heart conditions may be enabled. FIGS. 5A-5E conceptually illustrate the principles of detecting heart conditions using the blood augmentation pressure. Other similar techniques and algorithms may be used to similarly detect augmentation pressure. The time frame of two heart beats used in FIGS. 5A-5E is for purposes of illustration and clarity and the techniques and measurement may be continued over any number of heart beats or over any time frame. Example matching time segments for the first heart beat across FIGS. 5B-5C are identified by dotted lines and labels A, B, C and D for sake of comparison between the different representations of the data in each figure.

Figure 5A:
FIG. 5A is a diagram illustrating an electro-cardiogram signal over two heart beats.
Figure 5B:
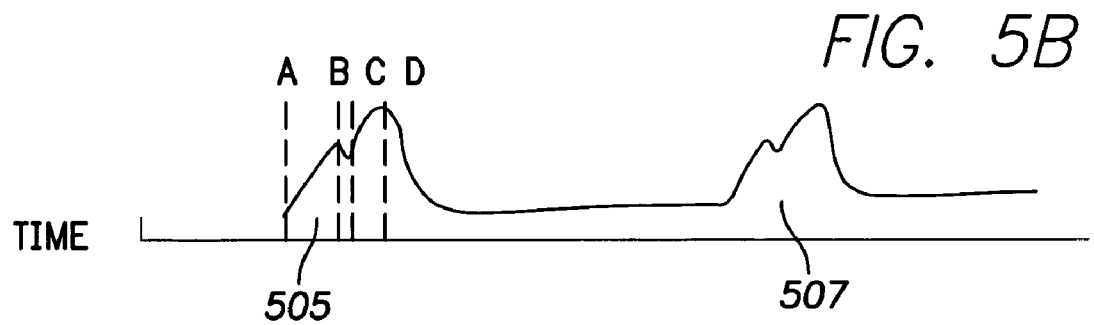
FIG. 5B is a diagram illustrating a blood pressure measurement over the two heart beats of FIG. 5A.
Figure 5C:
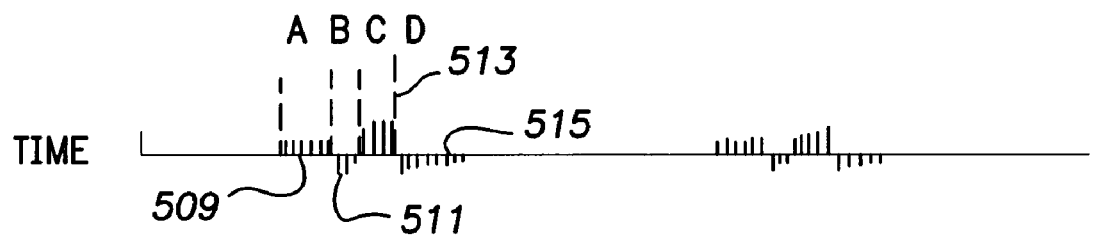
FIG. 5C is a diagram illustrating a derived or monitored degree of change in blood pressure over the time period of the two example heart beats of FIG. 5B.

FIG. 5A is a diagram of an electro-cardiogram (ECG) signal over the time frame of two example standard heart beats of a patient received by a monitoring and/or stimulation device. The first heart beat 501 and second heart beat 503 may each be described or characterized as PQRST waves. The example heart beats 501 and 503 are normal heartbeats for a patient. The heart beats 501 and 503 may be for a patient in an awakened state.

FIGS. 5B-5E are diagrams showing example measurements of blood pressure and related information in different representations over the time frame of the two example heart beats of the patient. FIG. 5B is a diagram of an example measurement of blood pressure over the time period of the two heart beats 501, 503. Each heart beat 501, 503 induces a related increase in blood pressure as shown by the first blood pressure pulse 505 corresponding to the first heart beat 501 and the second blood pressure pulse 507 corresponding to the second heart beat 503. Each blood pressure pulse 505, 507 exhibits the standard dual peak pattern including an augmentation pressure between a local minima between the peaks and the second peak.

FIG. 5C is a diagram representing a derived or monitored degree of change in blood pressure over the time period of the two example heart beats. The diagram shows the deviation from the previous reading of the blood pressure over the time space of the two heart beats 501, 503, the derivative of the slope of the signal at each sampling point or similar data representation indicating the change in the monitored blood pressure level.

These representations identify different phases of the blood pressure pulse. An initial phase 509 corresponds with the increase in blood pressure caused by the action of the atria of the heart that causes the initial spike in blood pressure in the heart. A second phase 511 corresponds to the decrease in blood pressure after the completion of the action of the atria and hitting an initial peak blood pressure in the first spike and before the action of the ventricles starts the second spike. A third phase 513 corresponds to the quick increase in blood pressure caused by the action of the ventricles creating the second spike in blood pressure. The fourth phase 515 corresponds to the decrease of the blood pressure toward the baseline pressure after the action of the ventricles completes and the second peak of blood pressure is reached. This set of phases repeats in each blood pressure pulse for each heartbeat.

The degree of changed detected in each reading may vary for each patient and each heart beat. General patterns in the change may be detected for different levels of activity and different circadian states for each patient during an initial calibration phase. The sampling rate for calculating the change in blood pressure may be constant over each blood pressure pulse to allow consistent measurements and for ease of comparison between measurements. Any sampling rate may be used and may set during calibration by a medical professional or under similar circumstances. Sampling may be synchronized using known heart rate information, blood pressure patterns, ECG patterns or similar information.

Figure 5D:
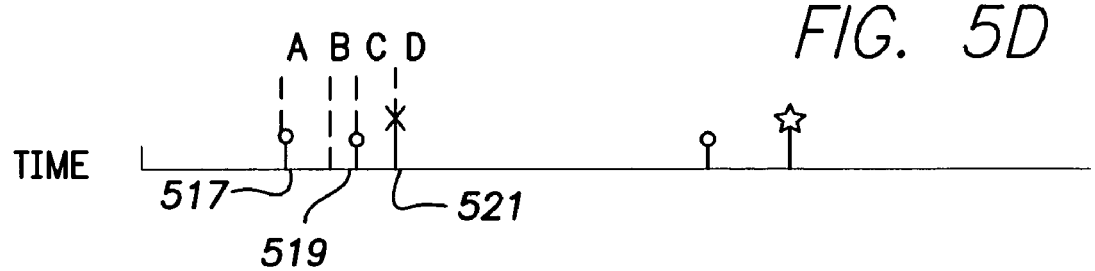
FIG. 5D is a diagram illustrating indicators of a start position of a blood pressure pulse and a blood pressure pulse peak for the two heart beats of FIG. 5C.

FIG. 5D is a diagram related to the diagram of 5C with key transition points identified for purposes of calculating the augmentation pressure. In one embodiment, a set of key points 517, 519 and 521 for each blood pressure pulse are identified by a pressure measurement analysis component or program to assist in calculating the augmentation pressure. Key points may be identified to flag important data in a sample set of blood pressure readings or calculated changes in blood pressure or similar data for use in calculating augmentation pressure for each blood pressure pulse.

For example, the detection of an increase in blood pressure or start of an initial phase may be flagged 517 to identify a data sample corresponding to the baseline blood pressure before the blood pressure pulse. A second data point 519 may be identified to mark the start of the subset of the sample data related to the augmentation pressure, which correlates with the third phase of the data discussed in relation to FIG. 5C. The second data point 519 may be detected by monitoring for what may be referred to as a zero crossing. A zero crossing may be a point in a set of sample data where values shift from positive to negative or from negative to positive. The data samples make a zero crossing at the start of the second and third phases, thus, detecting the second zero crossing in a sample data set can be used to determine the second data point 519. A third data point may be flagged 521 to identify the end of the third phase or the end of the augmentation pressure subset of data. This flagged data point may be used in combination with the second data point to identify the subset of data needed for calculating augmentation pressure. In another embodiment, data points may be flagged for the peak blood pressure and the local minima or start of the blood pressure pulse to identify data that can be used to subtract the blood pressure change in the blood pressure pulse corresponding to the first two phases from the peak blood pressure thereby deriving the augmentation pressure.

In other embodiments, other combinations of key points may be flagged and data points identified to determine the augmentation pressure. For example, the end of the third phase and the end of the second phase may be the only key points identified and the changes in pressure sampled between these key points summed to determine the augmentation pressure.

Figure 5E:
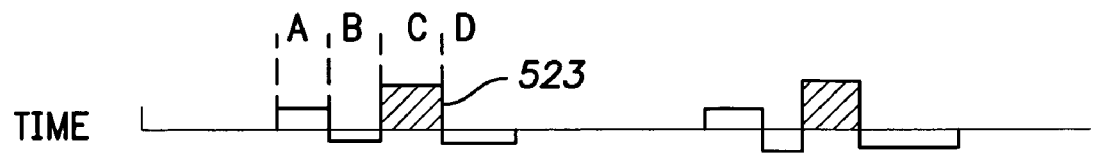
FIG. 5E is a diagram illustrating blood pressure levels over specific segments of the blood pressure pulse for the two heart beats of FIG. 5D.

FIG. 5E is a diagram of another example conceptual representation of blood pressure measurements that may be used to determine the augmentation pressure. In one embodiment, the data for each identified period may be averaged separately over time as represented by the squared signal. This calculation scheme may be used in conjunction with the tracking of change in pressure. The change in pressure data may be used to identify zero crossings to segment the data into the different phases. Then the blood pressure levels in each phase may be averaged and a calculation made based on the average of the third phase and the known length of the third phase to determine the augmentation pressure for a blood pressure pulse. For example, the area enclosed by squared wave and baseline for each phase may be calculated or the area of the third phase 523 may be calculated to produce an augmentation pressure or approximation of the augmentation pressure. In another embodiment, the diagram of FIG. 5E may be determined by using the maximum or minimum value in each phase. This embodiment generates a squared signal that envelops the data plotted in FIG. 5C.

The techniques and representations for determining the augmentation pressure for each blood pressure pulse are provided by example and not exhaustive. One skilled in the art would understand that known equivalents of these techniques for processing signal data to identify a subset of the signal may be used in combination or individually to determine augmentation pressure for each blood pressure pulse.

Figure 6:
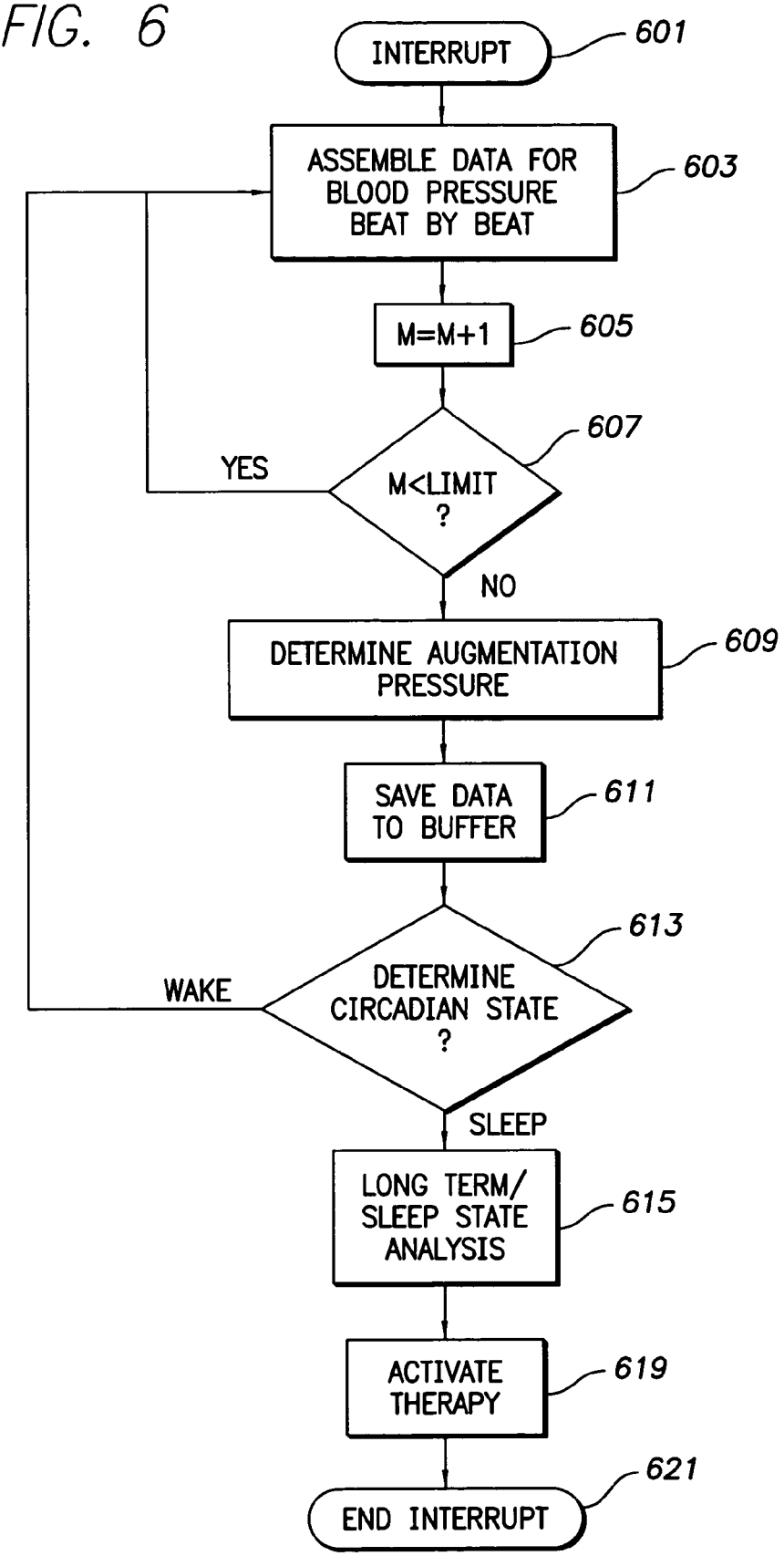
FIG. 6 is a diagram of one embodiment of a process for measuring and analyzing augmentation pressure to detect a circadian state or other heart conditions.

FIG. 6 is a flowchart of one embodiment of a process for determining and analyzing augmentation pressure data. In one embodiment, the process may be initiated by an interrupt (block 601) or other call to the process embodied in software/firmware executed by a general purpose processor or an application specific integrated circuit, other hardwired circuitry or similar structure. The interrupt or call to the process may be generated at a regular interval, arrival of new sample data or in response to similar events. In another embodiment, the process may be run continuously once initiated, wherein the processor may poll or similarly check for new sample data.

In one embodiment, upon activation the process may start the assembly of a beat by beat blood pressure data (block 603). The blood pressure data received from the sensors in the leads attached to the device may be collected, indexed or similarly stored in a temporary data structure or memory. The data received from the sensors may be analog or digital data representing an absolute blood pressure measurement, a relative blood pressure measurement or similar data. In one embodiment, the device and pressure analysis component may receive continuous real time data and may sample the data at a regular interval. In another embodiment, the device may receive intermittent data reading from the lead sensors.

In one embodiment, each sampled blood pressure measurement that is received or sampled may be individually averaged into a running total for a beat. In another embodiment, the data may be maintained individually in its entirety until the whole beat sampling is completed. The sampled data may be approximated, simplified or similarly processed to conserve storage space. The data may be selectively discarded to keep only that data identified as relevant to calculating the augmentation pressure.

The start of a beat may be identified by analyzing received blood pressure data to determine a key point, zero crossing or similar transition indicator. The assembly of the blood pressure data on a beat by beat basis may use an index M that corresponds to the number of samples to be taken during a heart beat. The index M, as well as the sampling frequency, may be set by a medical professional during calibration, fixed values, dynamically determined values responsive to transitions and trends in blood pressure or other heart conditions or similarly defined. After a sample has been incorporated into an average, tallied, identified as part of collection or similarly processed, the index may be increased (block 605). The assembly of the data into a moving average minimizes the effect of respiratory modulation on the blood pressure.

In one embodiment, after each sample is recorded or incorporated into the running average, tally or similar format, a check may be made to determine if a requisite or designated number of samples covering the heartbeat or a desired segment of the heartbeat has been collected (block 607). The check may be performed by comparing the current index to a threshold or similar limit designating the sample size. If the threshold or limit is exceeded or met the process may proceed to analyze the collected data (block 609). If the limit has not been exceeded or met then the collection process may continue by waiting for the next sample of data, the next interrupt indicating the availability of the data or similar event.

In one embodiment, after a designated amount of data has been collected, for example, the data may be used in a determination of augmentation pressure according to any of the techniques discussed above in relation to FIGS. 5A-5E or similar techniques (block 609). After the augmentation pressure has been determined for the beat, the augmentation pressure may be stored in a data buffer (block 611). The data buffer may be memory internal to the microcontroller or device or external to the microcontroller or device.

In one embodiment, after each time a new entry is recorded for augmentation pressure a determination of the circadian state of the patient may be conducted (block 613). The determination of the circadian state may be through an analysis of the augmentation pressure trend over the short term, comparison of the recent augmentation pressure reading as a histogram to a template or through similar processes.

Short term trend analysis may be based on a comparison of the current augmentation pressure or a recent average augmentation pressure with a dynamic or set threshold value or set of threshold values, a longer term average or similar values. Threshold values may be set by a medical professional or through a calibration process that determines the normal augmentation pressure in each circadian state for the patient. Upper or lower bounds of augmentation pressure may be set to detect sleeping or awakened states. For example, a threshold value may be set that is roughly fifty percent greater than the standard awakened augmentation pressure. If the current or recent average exceeds the threshold, then the patient is determined to be in a sleeping state.

In another embodiment, a running average of augmentation pressure is maintained for a preceding hour or similar window of time. A current augmentation pressure or recent average of five to ten minutes or a designated number of heart beats may be compared to the longer average. If the current augmentation pressure or recent average is more than approximately double the running average a sleep state transition has been detected. If the current augmentation pressure or recent average is half or less of the longer average then a transition from a sleep state to a wake state has been detected.

Figure 7:
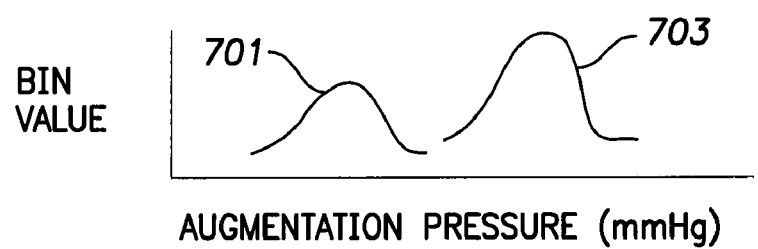
FIG. 7 is a diagram of an example set of blood pressure measurements as a histogram.

In a further example embodiment, histograms may be used to determine the circadian state of the patient. FIG. 7 is a diagram of one representation of collected augmentation pressure as a histogram. During calibration or a similar initial period, standard templates for the wake and sleep states of a patient may be determined. This may be accomplished by recording augmentation pressure measurements over a 24 hour period or a longer period. Charting the measurement into a histogram such as for individual augmentation pressure readings or blocks of augmentation pressure readings generates a template reflecting standard augmentation pressure levels in the wake and sleeping states.

For example, the standard augmentation pressure data for 24 hour period or longer may be charted as shown in FIG. 7. The charted data visually identifies two distinct ranges or groupings of augmentation pressure levels. The first range 701 corresponds to an awakened state. The second range 703 corresponds to a sleep state. The example histogram demonstrates that the wake state and sleep state have distinct ranges with most measurements falling in the middle of each range. The histogram can be used as a template for comparison with current augmentation pressure measurements or histograms generated from recent augmentation measurements. If a current value or histogram of recent measurements falls within one of the ranges identified by the template histogram then the current circadian state of the patient can be identified.

After a check of the circadian state is conducted, if the patient is in the wake stage continued monitoring of the augmentation pressure may take place. The process may wait for additional data samples, the next interrupt or a similar event. Running longer term averages and histograms may be updated to incorporate the current augmentation pressure measurement. In some embodiments, longer term analysis of collected augmentation pressure to detect or confirm hypertension or similar heart conditions may be performed. Other short term analysis may also be performed that relies on the augmentation pressure data. This long term and short term analysis is described in greater detail below.

In some embodiments, if the patient is determined to be in a sleep state, a long term analysis of the data may be performed and/or other short term analysis may be conducted. For example, an analysis of data based on the sleep state may be performed (block 615). For example, if a slowed heart rate is detected based on electro-cardiogram input or slowed breathing is detected from respiratory sensor data that would seem to indicate sleep apnea, the sleep apnea may be confirmed by an analysis of augmentation pressure data to determine that the patient is in a sleep state, has a higher than normal augmentation pressure or blood pressure for the sleep state or similar confirming data are present.

A long term analysis of the data may compare the current augmentation pressure, a recent average, a recent histogram or similar short term data with a long term average, long term histogram or similar data. 'Long term' may refer to a period of several hours, a day, several days or longer. For example, a comparison of short term data with long term data may be used to detect or confirm hypertension, hypotension or similar heart conditions.

Figure 8:
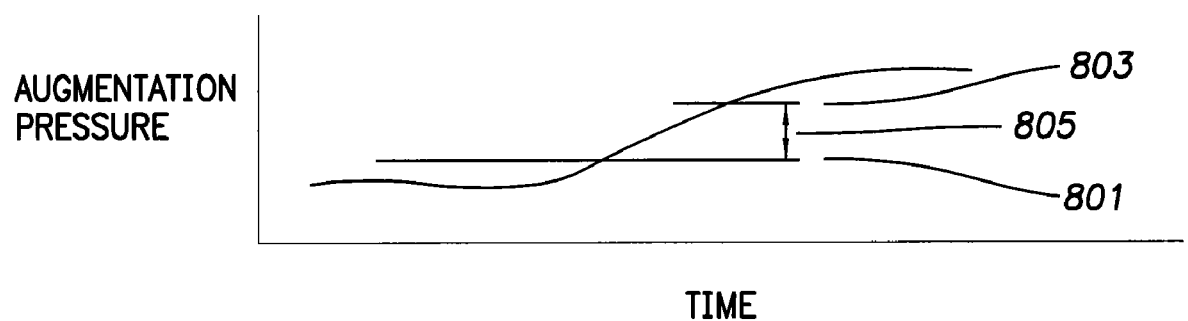
FIG. 8 is a diagram illustrating blood pressure tracking and threshold indicators.

FIG. 8 is a diagram illustrating one example technique for detecting hypertension. The diagram charts detected augmentation pressure in a patient over a time period of twenty four hours, multiple days, weeks or months. A recent short term collection of data 803 may be compared to a long term collection of data 801. For example, the short term collection 803 may be a short term average of augmentation pressure for a patient and the long term collection 801 may be a long term average of augmentation pressure for the patient. A difference 805 or delta between the short term and long term averages may be calculated. This value may be compared to a threshold value to determine if the patient is suffering from hypertension or similar condition. The threshold may be set by a medical professional or similarly determined. The threshold value may generally indicate a boundary or set of boundaries within which normal variations in augmentation pressure are expected, normal or healthy. Crossing the boundary may indicate that the deviation from the normal range of the patient is a result of a serious heart condition such as hypertension.

If a particular condition is detected, then the monitoring and/or stimulation device may activate the appropriate therapy for the condition (block 619). In the case of a detected change in circadian state, the activation of therapy may include the changing of the mode of operation for the monitoring and/or stimulation device from an awake mode to a sleep mode based on the circadian state detected by the process. For example, the stimulation pattern (e.g., A-A, A-V or V-V timing) for a sleeping patient may be slower than that of an active awake patient.

If a condition such as sleep apnea or hypertension is detected then other types of therapy may be activated or an alarm or similar indicator may be set to alert the patient or and attending medical professionals. If appropriate, stimulation patterns or similar therapy may be altered to alleviate a detected condition. For example, pacing (e.g. of A-A, A-V or V-V signals) may be increased to counteract the effects of sleep apnea.

After the activation of therapy, setting of indictors alarms or similar actions are taken based on analysis of the received augmentation pressure data, the process may end and the associated interrupt cleared (block 621). The process may be reinitiated by the next interrupt or similar event. In another embodiment, the process is not interrupt based. The process may be a continuous process. The continuous process may poll or similarly query for new data periodically.

It should be appreciated that the various components and techniques described herein may be incorporated in an apparatus (e.g., a stimulation device, a lead, etc.) independently of the other components and techniques. For example, an apparatus incorporating the teachings herein may include various combinations of these components and techniques. Thus, not all of the components and techniques described herein may be employed in every such apparatus.

Different embodiments of the stimulation device may include a variety of hardware and software processing components. In some embodiments, hardware components such as processors, controllers, state machines and/or logic may be used to implement the described components or circuits. In some embodiments, code such as software or firmware executing on one or more processing devices may be used to implement one or more of the described operations or components.

The components and functions described herein may be connected/coupled in many different ways. The manner in which this is done may depend, in part, on whether and how the components are separated from the other components. In some embodiments some of the connections/couplings represented by the lead lines in the drawings may be in an integrated circuit, on a circuit board or implemented as discrete wires.

The signals discussed herein may take several forms. For example, in some embodiments a signal may be an electrical signal transmitted over a wire while other signals may consist of wireless signals transmitted through space. In addition, a group of signals may be collectively referred to as a signal herein.

The signals discussed above also may take the form of data. For example, in some embodiments an application program may send a signal to another application program. Such a signal may be stored in a data memory.

In summary, the invention described herein generally relates to an improved monitoring and/or stimulation apparatus and sensor processing method. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A device comprising:
   an implantable housing;
   a lead coupled to the implantable housing;
   a sensor coupled to the lead, the sensor to generate a signal indicating blood pressure level in a heart of a patient;
   a pressure measurement processing component to analyze the signal and determine an augmentation pressure; and
   a data storage circuit to store augmentation pressure data;
   wherein the pressure measurement processing component compares changes in augmentation pressure to a threshold value.

2. The device of claim 1, wherein the pressure measurement processing component analyzes augmentation pressure data and determines a circadian state for the patient.

3. The device of claim 2, further comprising:
   a pacing circuit to generate pacing signals for the heart based on an indicator of the circadian state received from the pressure measurement processing component.

4. The device of claim 2, wherein the pressure measurement processing component generates a histogram of augmentation pressure.

5. The device of claim 1, wherein the pressure measurement processing component analyzes augmentation pressure data to detect hypertension.

6. The device of claim 1 wherein the pressure measurement processing component determines two different augmentation pressure measurements over time and changes in augmentation pressure comprises the difference between the two determined pressure measurements.

7. The device of claim 6 wherein a first of the two augmentation pressure measurements is based on a first plurality of determined augmentation pressures and a second of the two augmentation pressure measurements is based on a second plurality of determined augmentation pressures.

8. The device of claim 7 wherein the first augmentation pressure measurement is a average of the first plurality of augmentation pressures.

9. The device of claim 7 wherein the second augmentation pressure measurement is a average of the second plurality of augmentation pressures.

10. The device of claim 7 wherein:
    the first plurality of determined augmentation pressures are based on blood pressure level signals generated during a first period of time; and
    the second plurality of determined augmentation pressures are based on blood pressure level signals generated during a second period of time, different from the first period of time.

11. The device of claim 10 wherein the first period of time is shorter than the second period of time.

* * * * *